US010765311B2

(12) United States Patent
Masket (10) Patent No.: US 10,765,311 B2
(45) Date of Patent: Sep. 8, 2020

(54) EYE PATCH AND RELATED METHOD (71) Applicant: Barbara Masket, Los Angeles, CA (US)

(72) Inventor: Barbara Masket, Los Angeles, CA (US)

( * ) Notice: Subject to any disclaimer, the term of this patent is extended or adjusted under 35 U.S.C. 154(b) by 0 days.

(21) Appl. No.: 14/036,555

(22) Filed: Sep. 25, 2013

(65) Prior Publication Data

US 2015/0085257 A1    Mar. 26, 2015

(51) Int. Cl.
*A61B 3/02*    (2006.01)
*A61F 13/12*    (2006.01)

(52) U.S. Cl.
CPC .............. *A61B 3/02* (2013.01); *A61F 13/124* (2013.01); *Y10T 156/1036* (2015.01)

(58) Field of Classification Search
CPC ...... A61F 9/04; A61F 9/00; A61F 9/06; A61F 9/022; A61F 9/062; A61F 13/12; A61F 13/124; A61F 13/023; G02C 7/108; A61B 3/02; Y10T 156/1036
USPC ........ 351/159, 65, 222, 44, 41; 2/12, 14, 15, 2/431, 432; 128/858
See application file for complete search history.

(56) References Cited

U.S. PATENT DOCUMENTS 4,793,002 A * 12/1988 Simon ....................... A61F 9/04
2/15
4,793,003 A  12/1988 Riedel et al.
5,191,897 A * 3/1993 Meshel .................... A61B 3/00
128/858
5,970,515 A  10/1999 Fishbaugh
6,149,615 A  11/2000 Gallamore
7,052,130 B2 * 5/2006 Fishbaugh ................ A61F 9/04
2/12

(Continued)

FOREIGN PATENT DOCUMENTS

| JP | 3056162 U | 2/1999 |
| JP | 2002526199 A | 8/2002 |
| JP | 2004065892 A | 3/2004 |

OTHER PUBLICATIONS

The International Bureau of WIPO, International Preliminary Report on Patentability, International Application No. PCT/US2014/057153, dated Apr. 7, 2016 (7 pages).

(Continued)

*Primary Examiner* — Stephone B Allen
*Assistant Examiner* — Rahman Abdur
(74) *Attorney, Agent, or Firm* — Wood Herron & Evans LLP (57) ABSTRACT

An eye patch includes a single layer substrate comprising a sheet of material having a first region and a second region. An outer edge extends around the substrate and a slit extends through the substrate so as to form a first flap and a second flap. A first adhesive portion is applied to the substrate near the first region such that the first and second flaps each receive part of the first adhesive portion. A second adhesive portion is applied to the substrate near the second region, and the second adhesive portion is discontinuous with the first adhesive portion. The first and second flaps are configured to be placed into an overlapping arrangement and adhered together by the first adhesive portion to give the eye patch a generally cupped shape. The first and second adhesive portions provide two locations for adhering the eye patch a patient's face.

15 Claims, 4 Drawing Sheets

(56) References Cited

U.S. PATENT DOCUMENTS

RE39,896 E      10/2007    Arnold et al.
2005/0140923 A1    6/2005    Fishbaugh
2011/0034849 A1*   2/2011    Cooks .................. A61F 13/124
                                                                602/74

OTHER PUBLICATIONS

European Patent Office, International Search Report and Written Opinion of the International Searching Authority, International Application No. PCT/US2014/057153, dated Jan. 19, 2015 (9 pages).

Nexcare, Opticlude Orthoptic Eye Patch, screen shot retrieved from http://www.soap.com/p/nexcare-opticlude-tm-orthoptic-eyepatch-regular-58035 on May 29, 2013 (1 page).

CCT Coating and Converting Technologies, M1675-80-54 Permanent/Removable DC Acrylic PSA Tape Product Sheet, rev. date Jul. 8, 2013 (1 page).

European Patent Office, Examination Report, Application No. 14781393.5, dated Oct. 17, 2017 (5 pages).

Japanese Patent Office, Office Action, Application No. 2016-518101, dated Jun. 25, 2018 (10 pages).

\* cited by examiner

EYE PATCH AND RELATED METHOD

FIELD OF THE INVENTION

The present invention relates generally to devices for occluding an eye and, more particularly, to disposable eye patches.

BACKGROUND OF THE INVENTION

Devices for occluding, or blocking, a patient's eye are used for several types of clinical procedures. For example, such devices are commonly used during monocular eye examinations to test the differences in visual acuity between a patient's eyes. Occluding devices can be non-disposable or disposable, but there are potential problems associated with each.

A common non-disposable occluding device used in monocular eye testing procedures is generally paddle-shaped and is held up to a patient's eye to occlude the eye. Either a clinician or the patient must hold this type of occluding device. This may be undesirable, however, because when the clinician holds the occluding device, the clinician's ability to move relative to the patient during a procedure is limited. In addition, elderly patients or children may have difficulty holding the occluding device for the necessary duration of the procedure. In addition, this type of occluding device presents the risk of transferring diseases because the occluding device is reused, and may come into contact with eye secretions of various patients.

In another type of non-disposable occluding device, a fabric patch is held over the patient's eye by an elastic band placed around the patient's head, similar in appearance to a conventional "pirate's patch." Typically, this type of patch is used in conjunction with a piece of tissue placed between the patch and the patient's eye, and the tissue remains in compressive contact with the patient's eyelid while the patch is worn. Such patches are basically flat, however, and offer limited adjustment, other than the tightness around the patient's head. In addition, after this type of patch is removed, the patient's eye previously covered by the patch takes a period of time to adjust following its compression with the tissue and the patch.

A disposable occluding device is described in U.S. Pat. No. 6,149,615 to Gallamore, which is directed to an eye patch that can be used for the treatment of Amblyopia, or lazy eye. Gallamore discloses that patches are placed over a patient's good eye to regain visual function in the other eye, and that such patches may be worn for months at a time. The patient's eye is closed while the patch is worn. Gallamore's eye patch includes a foam pad adhered to an outer membrane, which extends beyond the periphery of the foam pad. The outer membrane of Gallamore's eye patch includes adhesive entirely surrounding the foam pad to securely adhere the eye patch to a patient's face while completely obscuring the patient's vision. Gallamore describes that the foam pad is required to support the eye patch in a concavo-convex shape. It is neither economical nor easy to use this type of eye patch for use in eye examination procedures, however, because occluding devices for eye examinations do not require foam pads or adhering an occluder device in a way that completely obscure a patient's vision in the occluded eye.

Another example of a disposable occluding device is shown in U.S. Pat. No. 5,191,897 to Meshel, which is directed to a flat eye occluder that is temporarily adhered to a patient's face or spectacles. Meshel's occluder is configured to be adhered to a patient's face above the eye, and drape down over the eye. After use, the occluder is removed. Such an occluder may contact the patient's eye, eyelid, or eyelashes however, and cause some degree of interference with the eye or some degree of discomfort for the patient due to the contact. This is especially likely if the patient has long or bushy eyelashes. For example, prostaglandin analog (PGA) medications are used for the treatment of glaucoma and may cause eyelash growth. Patients who have received PGA treatments and who have long or bushy eyelashes may find that occluding devices such as Meshel's occluder cause interference or discomfort during use.

SUMMARY OF THE INVENTION

The present invention overcomes the foregoing problems and other shortcomings and drawbacks of known eye patches, including known disposable eye patches. While the present invention will be described in connection with certain embodiments, it will be understood that the present invention is not limited to these embodiments. To the contrary, this invention includes all alternatives, modifications, and equivalents as may be included within the spirit and scope of the present invention.

According to one embodiment of the present invention, an eye patch includes a single-layer substrate comprising a sheet of material having a first region and a second region. An outer edge extends around the substrate and a slit extends through the substrate from a point on the outer edge of the first region to an interior point of the substrate so as to form a first flap and a second flap. A first adhesive portion is applied to the substrate near the first region such that the first and second flaps each receive part of the first adhesive portion. A second adhesive portion is applied to the substrate near the second region, and the second adhesive portion is discontinuous with the first adhesive portion. The first and second flaps are configured to be placed into an overlapping arrangement and adhered together by the first adhesive portion to give the eye patch a generally cupped shape. The first and second adhesive portions provide two locations for adhering the eye patch to the periorbital tissue surrounding an eye.

According to another embodiment of the invention, a method is provided for forming a cupped shaped eye patch from a single-layer substrate comprising a sheet of material having a first region and a second region. The substrate includes an outer edge extending around the substrate and a slit extending through the substrate from a point on the outer edge of the first region to an interior point of the substrate so as to form a first flap and a second flap. The eye patch further includes a first adhesive portion applied to the substrate near the first region such that the first and second flaps each receive part of the first adhesive portion, and a second adhesive portion applied to the substrate near the second region. The second adhesive portion is discontinuous with the first adhesive portion. The method includes placing a first flap of the eye patch in an overlapping arrangement with a second flap of the eye patch so as to deform the eye patch from a generally planar shape to a cupped shape. The method further includes adhering the first flap to the second flap in the overlapping arrangement.

According to another embodiment of the invention, a roll of eye patches is provided and includes a roll of backing material and a plurality of eye patches releasably attached to the backing material. Each eye patch includes a single-layer substrate comprising a sheet of material having a first region and a second region. An outer edge extends around the substrate and a slit extends through the substrate from a point on the outer edge of the first region to an interior point of the substrate so as to form a first flap and a second flap. A first adhesive portion is applied to the substrate near the first region such that the first and second flaps each receive part of the first adhesive portion. A second adhesive portion is applied to the substrate near the second region, and the second adhesive portion is discontinuous with the first adhesive portion. The first and second flaps are configured to be placed into an overlapping arrangement and adhered together by the first adhesive portion to give the eye patch a generally cupped shape. The first and second adhesive portions provide two locations for adhering the eye patch to the periorbital tissue surrounding an eye.

The above and other objectives of the present invention shall be made apparent from the accompanying drawings and description thereof.

BRIEF DESCRIPTION OF THE DRAWINGS

The accompanying drawings, which are incorporated in and constitute a part of this specification, illustrate embodiments of the present invention and, together with a general description of the invention given above, and the detailed description of the embodiments given below, serve to explain the principles of the present invention.

DETAILED DESCRIPTION OF THE INVENTION

Turning now to the figures, and in particular to FIGS. 1-4, an eye patch 10 is shown according to one embodiment of the present invention. As will be apparent from the following description, the eye patch 10 is useful as a disposable device for temporarily occluding, or blocking, a patient's eye during an eye examination procedure. In addition, the eye patch 10 includes features that provide a contoured shape which does not place pressure on the patient's eyelid or restrict eye movement. In particular, the eye patch 10 is readily transformed from a generally planar, or flat shape, to a cupped shape. The cupped shape allows the eye patch 10 to avoid contacting the patient's eyelid.

Figure 1:
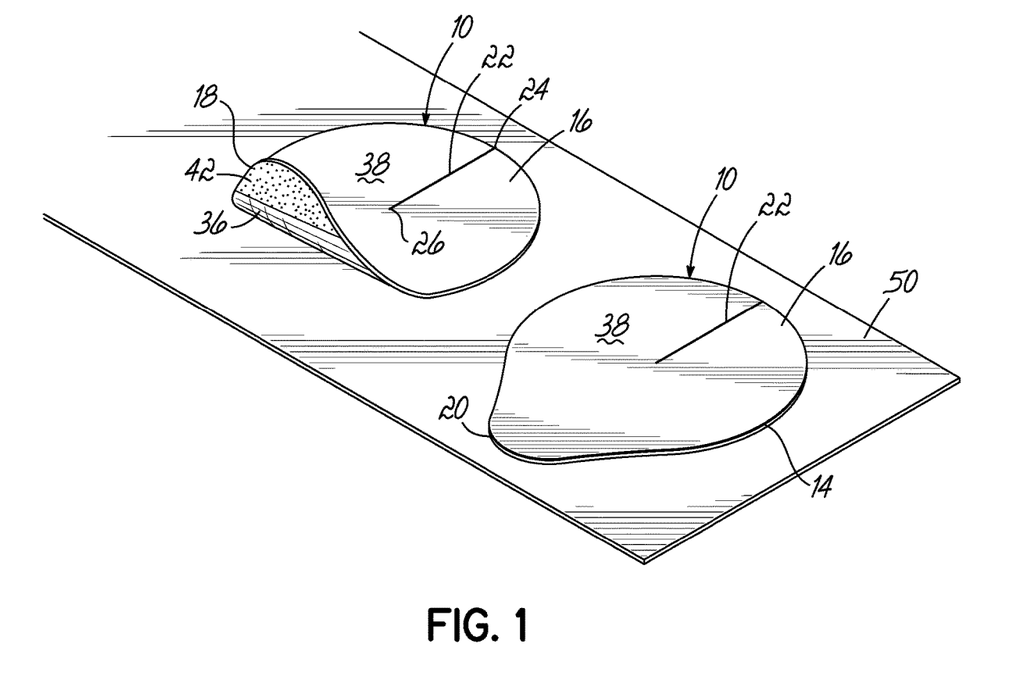
FIG. 1 is an isometric view showing two eye patches according to one embodiment of the present invention.
Figure 2:
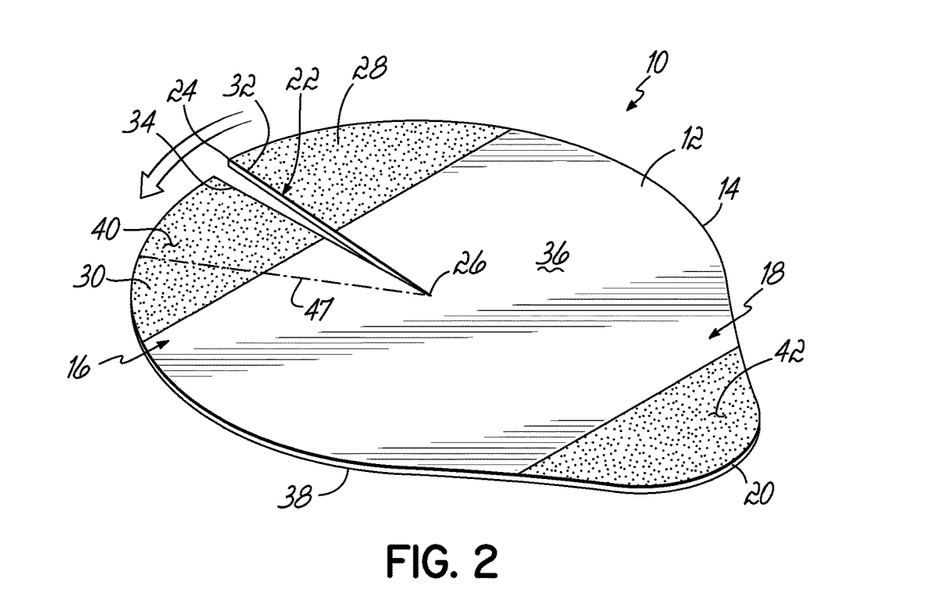
FIG. 2 is an isometric view showing an eye patch according to one embodiment of the present invention, and with a first flap thereof lifted relative to a second flap.

The eye patch 10 generally includes a single-layer substrate 12, which, in the embodiment shown, includes a sheet of material having a teardrop shape. An outer edge 14 extends around the periphery of the substrate 12. The substrate 12 includes a first region 16 and a second region 18. The first region is located generally opposite the second region 18, and the second region 18 may be near a tapered tab 20 of the teardrop shape. The substrate 12 has a generally planar shape, so as to be able to be placed in the generally flat configuration as shown in FIGS. 1 and 2. The substrate 12 is also generally flexible, and can be deformed so as to no longer have a planar shape, such as to provide a depth element to the eye patch 10, as will be described in greater detail below.

The substrate 12 includes a slit 22. In particular, the slit 22 extends through the substrate 12 from a point 24 on the outer edge 14 to an interior point 26 of the substrate 12. The point 24 is generally on the outer edge 14 of the first region 16, and the interior point 26 is generally centrally located within the substrate 12. The slit 22 forms first and second flaps 28, 30. The flaps 28, 30 have respective facing flap edges 32, 34 at the location of the slit 22.

The substrate 12 has two opposed sides: a first side 36 and a second side 38. The first side 36 generally faces a patient's eye when the patch 10 is applied to a patient's face. The second side 38 faces away from the patient when the patch 10 is applied to the patient's face.

The eye patch 10 includes a first adhesive portion 40 and a second adhesive portion 42. The adhesive portions 40, 42 are applied to the first side 36 of the substrate 12, as shown in FIG. 2. In particular, the first adhesive portion 40 is applied to the substrate 12 near the first region 16, and the second adhesive portion 42 is applied to the substrate 12 near the second region 18. The first adhesive portion 40 is distinct from, and discontinuous with, the second adhesive portion 42. As shown, the slit 22 extends through the first adhesive portion 40. Also, the first adhesive portion 40 is generally opposite the second adhesive portion 42, and the substrate 12 is generally free of adhesive between the first and second adhesive portions 40, 42.

The first and second adhesive portions 40, 42 are used to temporarily adhere the eye patch 10 to a patient's face. In addition, the first adhesive portion 40 is also used to adhere the first and second flaps 28, 30 together when the substrate 12 is deformed to a configuration that provides the eye patch 10 with a depth element.

Figure 3:
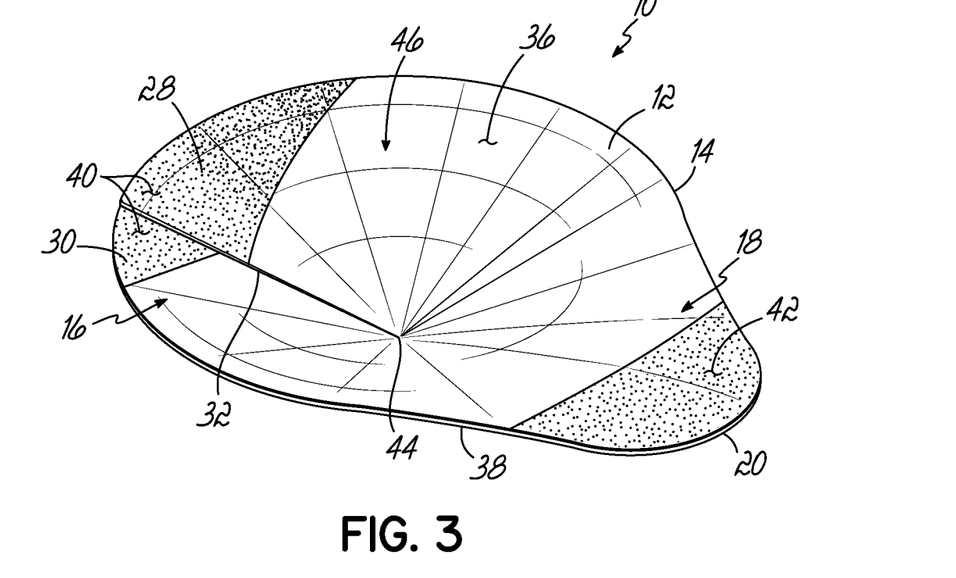
FIG. 3 is an isometric view showing the eye patch of FIG. 2 after the first and second flaps have been placed into an overlapping arrangement and adhered together.
Figure 4:
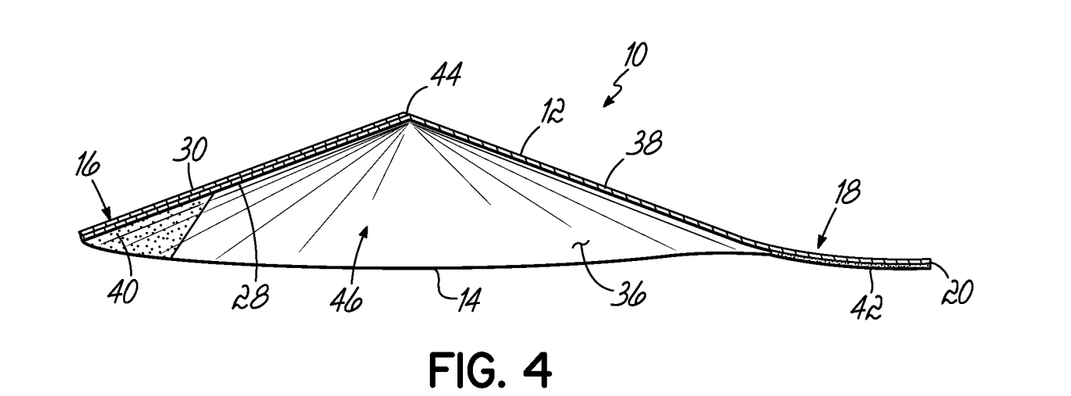
FIG. 4 is a transverse cross section view showing the eye patch of FIG. 3.

The eye patch 10 is configured to allow the first and second flaps 28, 30 to be placed into an overlapping arrangement and adhered together, as shown in FIGS. 3 and 4. For example, the substrate 12 can be deformed so that the second side 38 of the first flap 28 is placed into confronting relationship with the first side 36 of the second flap 30. Then, the second side 38 of the first flap 28 can be pressed into contacting engagement with the first adhesive portion 40 on the first side 36 of the second flap 30, thereby causing the first and second flaps 28, 30 to be adhered together by the first adhesive portion 40, as shown in FIG. 3. Alternatively, the substrate 12 can be deformed so that the first side 36 of the first flap 28 is placed into confronting relationship with the second side 38 of the second flap 30. Then, the second side 38 of the second flap 30 can be pressed into contacting engagement with the first adhesive portion 40 on the first side 36 of the first flap 28, thereby causing the first and second flaps 28, 30 to be adhered together by the first adhesive portion 40.

Once the substrate 12 is so deformed, and the first and second flaps 28, 30 are adhered to one another, the eye patch 10 is no longer planar, and has a depth, as shown in FIGS. 3 and 4. In particular, the eye patch 10 takes on a contoured cupped shape, somewhat resembling an open cone. A point 44 of the cone is formed at the interior point 26, and an interior space 46 is formed in the depth between the outer edge 14 and the point 44. The interior space 46 provides a clearance over a patient's eye when the eye patch 10 is applied to the patient's face, as will be described below. The extent of the depth of the eye patch 10 can be chosen by adjusting the extent of the overlap of the first and second flaps 28, 30. For example, a shallow depth is created when the first and second flaps 28, 30 overlap to a lesser extent, and a deeper depth is created when the first and second flaps 28, 30 overlap to a greater extent. In some embodiments, the first and second flaps 28, 30 may be separated after being adhered together in order to adjust the extent of the overlap and change the depth of the eye patch 10. The eye patch 10 is essentially self supporting once it is put into the cupped shape described above, and does not require additional structure to retain its cupped shape.

Optionally, and as shown in FIG. 2, the substrate 12 can include one or more markings 47 for indicating flap edge alignment positions for placing the first and second flaps 28, 30 into the overlapping arrangement. For example, the markings 47 can be provided on the first side 36 of the substrate 12 to show suitable positions for aligning the flap edges 32, 34 when the first and second flaps 28, 30 are placed into the overlapping arrangement and adhered together.

The substrate 12 may be formed of a paper material or any other suitable material that has sufficient rigidity to retain the eye patch 10 in the cupped shape described above. Advantageously, the eye patch 10 is disposable, and is formed of a material appropriate for disposal after a single use. In some embodiments, the substrate 12 can be Rainbow Duo-Finish Economy Kraft Paper, which is generally commercially available.

The first and second adhesive portions 40, 42 may be formed of or include any suitable material. For example, the first and second adhesive portions 40, 42 may include pressure sensitive adhesive that tends to stick to an object when the part having the adhesive portion is pressed against the object. For example, the first and second adhesive portions 40, 42 may be made of a material that permits the eye patch 10 to both (1) stick to a patient's face for a temporary duration during a procedure, and (2) be easily removed from the patient's face when the procedure is completed. In some embodiments, the first and second adhesive portions 40, 42 can include M1675 adhesive tape, which is commercially available from CCT (Coating and Converting Technologies) of Philadelphia, Pa.

Figure 5:
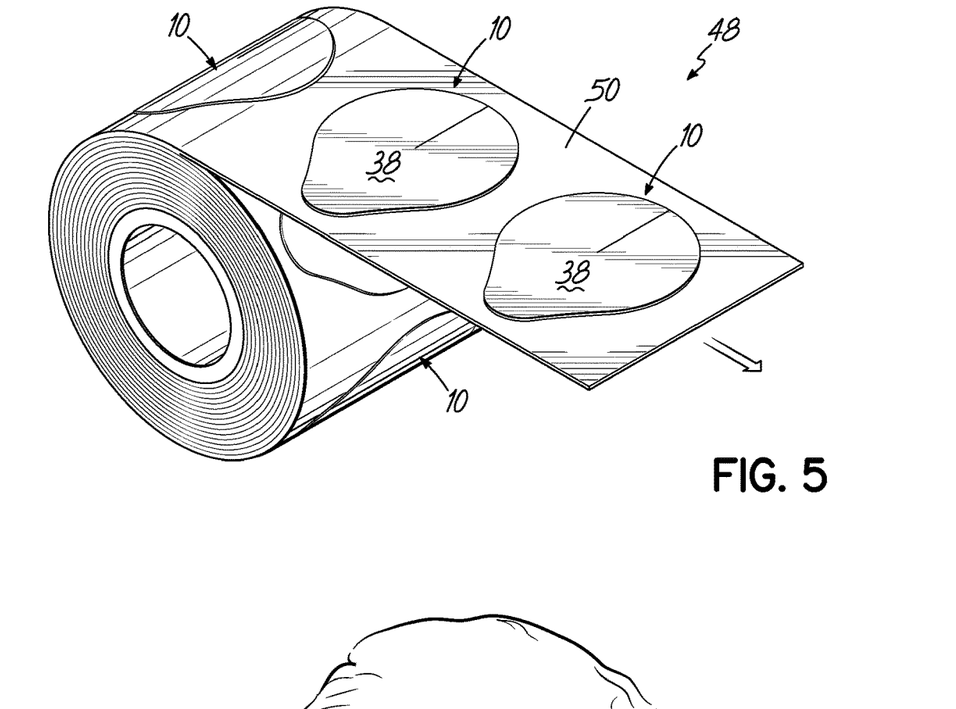
FIG. 5 is an isometric view showing a roll of eye patches according to one embodiment of the present invention.

As shown in FIG. 5, a roll of eye patches 48 can be provided that includes a plurality of the eye patches 10. In particular, the roll 48 includes a roll of backing material 50, and the eye patches 10 are releasably attached to the backing material 50. In particular, the first and second adhesive portions 40, 42 secure the eye patches 10 to the backing material 50. As shown, the eye patches 10 are provided on the roll 48 in their planar condition. Optionally, the backing material 50 may include perforations between eye patches 10, thereby allowing a section of the backing material 50 having one or more eye patches 10 to be easily separated from the roll 48. In some embodiments, the backing material 50 can be 54.7# White Glassine Liner L-3, which is commercially available from Sil Tech of Miamisburg, Ohio (Product Item #9019054).

An eye patch 10 can be removed from the roll 48 and deformed to give it a depth element, as described above. In particular, the first and second adhesive portions 40, 42 are separated from the backing material 50, and then the flaps 28, 30 are placed into an overlapping arrangement and adhered together. The eye patch 10 is then prepared for applying to a patient's face.

Figure 6:
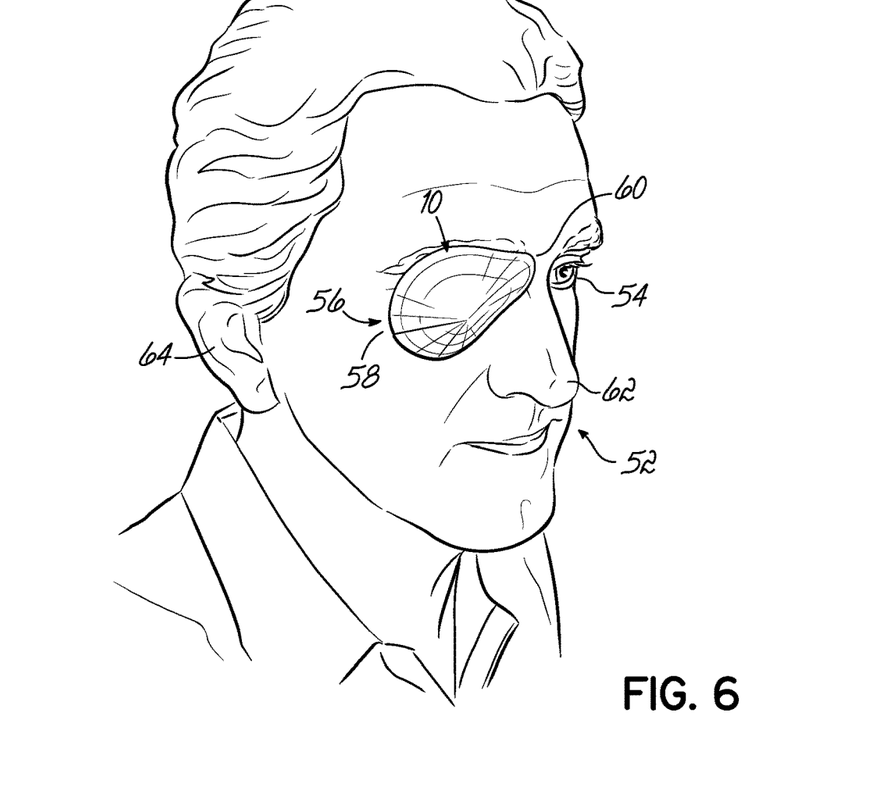
FIG. 6 is an isometric environmental view showing an eye patch placed on a patient's face.
Figure 7:
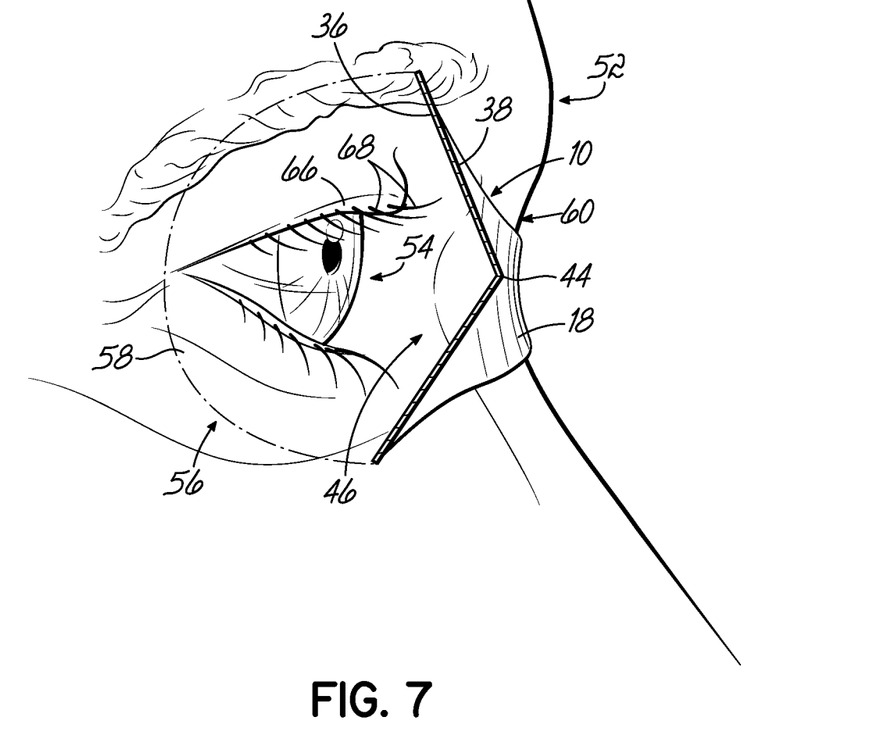
FIG. 7 is a side view in partial cross section showing the eye patch of FIG. 6.

Turning to FIGS. 6 and 7, an eye patch 10 is shown applied to a patient's face 52. In particular, the eye patch 10 is positioned on the face 52 to occlude the patient's eye 54, which can remain open with the eye patch 10 present. The eye patch 10 is adhered at two locations to the periorbital tissue 56 surrounding the eye 54. Specifically, the eye patch 10 is adhered at a first location 58 by the first adhesive portion 40, and at a second location 60 by the second adhesive portion 42. For example and as shown, the first location 58 can be located between the patient's eye 54 and ear 64, and the second location 60 can be located between the patient's eye 54 and nose 62. Other suitable locations are also possible. The eye patch 10 is unadhered to the periorbital tissue 56 other than at the first and second locations 58, 60.

Because the eye patch 10 has a cupped shape, the substrate 12 does not contact the patient's eye 54. Particularly, the first side 36 of the substrate 12, which faces the eye 54, is spaced from and does not place pressure on the patient's eyelid 66 or otherwise restrict eye movement. Moreover, the eye patch 10 does not contact or interfere with the patient's eyelashes 68. Advantageously, the patient can keep the eye 54 open during a procedure, which is the preferred method for many eye examination procedures.

After a procedure, the eye patch 10 is easily removed from the patient's face. Specifically, the eye patch 10 is separated from the patient's face at the first and second locations 58, 60. Then, the eye patch 10 can be discarded. A new eye patch 10 can be used for each new patient undergoing an eye examination.

While the present invention has been illustrated by a description of various embodiments, and while these embodiments have been described in some detail, they are not intended to restrict or in any way limit the scope of the appended claims to such detail. Additional advantages and modifications will readily appear to those skilled in the art. The various features of the invention may be used alone or in any combination depending on the needs and preferences of the user. This has been a description of the present invention, along with methods of practicing the present invention as currently known. However, the invention itself should only be defined by the appended claims.

What is claimed is:
1. An eye patch, comprising:
  a single layer substrate comprising a sheet of material having a first region and a second region, the substrate including an outer edge extending around the substrate and a slit defined entirely by a single line extending through the substrate from a point on the outer edge of the first region to an interior point of the substrate so as to form a first flap and a second flap,
  a first adhesive portion applied to the substrate near the first region such that the first and second flaps each receive part of the first adhesive portion with the slit extending between the respective parts of the first adhesive portion received on the first and second flaps so that the respective parts of the first adhesive portion are positioned directly on opposite sides of the slit, and adjacent the slit, with the slit extending therebetween, and
  a second adhesive portion applied to the substrate near the second region, the second adhesive portion being discontinuous with the first adhesive portion,
  wherein the first and second flaps are configured to be placed into an overlapping arrangement and adhered together by the first adhesive portion to give the eye patch a generally cupped shape, and wherein the first and second adhesive portions provide two locations, and the eye patch is sized and shaped, for adhering the eye patch to the periorbital tissue located on opposite sides of an eye so as to occlude the eye, and further wherein the substrate is rounded near the first region and enlarged relative to the second region which is tapered at a tapered tab located near the second region in both a planar and cupped form of the eye patch.

2. The eye patch of claim 1, wherein the substrate is generally planar.

3. The eye patch of claim 1, wherein the substrate comprises a paper material.

4. The eye patch of claim 1, wherein the first and second flaps include respective facing first and second flap edges, and wherein the substrate includes one or more markings for indicating one or more flap edge alignment positions for placing the first and second flaps into the overlapping arrangement.

5. The eye patch of claim 1, wherein the slit extends through the first adhesive portion.

6. The eye patch of claim 1, wherein the first adhesive portion is located generally opposite the second adhesive portion.

7. The eye patch of claim 1, wherein the substrate is free of adhesive between the first and second adhesive portions.

8. The eye patch of claim 1, wherein the substrate has sufficient rigidity to retain the eye patch in the cupped shape.

9. A method of forming a cupped shaped eye patch from a single-layer substrate comprising a sheet of material having a first region and a second region, the substrate including an outer edge extending around the substrate and a slit defined entirely by a single line extending through the substrate from a point on the outer edge of the first region to an interior point of the substrate so as to form a first flap and a second flap, the eye patch further including a first adhesive portion applied to the substrate near the first region such that the first and second flaps each receive part of the first adhesive portion with the slit extending between the respective parts of the first adhesive portion received on the first and second flaps so that the respective parts of the first adhesive portion are positioned directly on opposite sides of the slit, and adjacent the slit, with the slit extending therebetween, and a second adhesive portion applied to the substrate near the second region, the second adhesive portion being discontinuous with the first adhesive portion the substrate being rounded near the first region and enlarged relative to the second region which is tapered at a tapered tab located near the second region in both a planar and cupped form of the eye patch, the method comprising:

placing a first flap of the eye patch in an overlapping arrangement with a second flap of the eye patch so as to deform the eye patch from a generally planar shape to a cupped shape, adhering the first flap to the second flap in the overlapping arrangement so that the eye patch is configured to be adhered to the periorbital tissue located on opposite sides of the eye so as to occlude an eye when the eye patch is adhered to the periorbital tissue surrounding the eye.

10. The method of claim 9, wherein the first flap and second flap are adhered together with the first adhesive portion.

11. The method of claim 10, wherein the eye patch is adhered to the first location with the first adhesive portion, and wherein the eye patch is adhered to the second location with the second adhesive portion.

12. The method of claim 9, further comprising:
removing the eye patch from a backing material before placing the first and second flaps in an overlapping arrangement.

13. The method of claim 12, wherein removing the eye patch from a backing material includes separating the first adhesive portion and the second adhesive portion from a roll of the backing material.

14. A roll of eye patches, comprising:
a roll of backing material, and
a plurality of eye patches releasably attached to the backing material, each eye patch including:
a single layer substrate comprising a sheet of material having a first region and a second region, the substrate including an outer edge extending around the substrate and a slit defined entirely by a single line extending through the substrate from a point on the outer edge of the first region to an interior point of the substrate so as to form a first flap and a second flap,
a first adhesive portion applied to the substrate near the first region such that the first and second flaps each receive part of the first adhesive portion with the slit extending between the respective parts of the first adhesive portion received on the first and second flaps so that the respective parts of the first adhesive portion are positioned directly on opposite sides of the slit, and adjacent the slit, with the slit extending therebetween, and
a second adhesive portion applied to the substrate near the second region, the second adhesive portion being discontinuous with the first adhesive portion,
wherein the first and second flaps are configured to be placed into an overlapping arrangement and adhered together by the first adhesive portion to give the eye patch a generally cupped shape, and wherein the first and second adhesive portions provide two locations, and the eye patch being sized and shaped, for adhering the eye patch to the periorbital tissue located on opposite sides of an eye so as to occlude the eye,
and further wherein the substrate is rounded near the first region and enlarged relative to the second region which is tapered at a tapered tab located near the second region in both a planar and cupped form of the eye patch.

15. An eye patch, comprising:
a single layer substrate comprising a sheet of material having a first region and a second region, the substrate including an outer edge extending around the substrate and a slit defined entirely by a single line extending through the substrate from a point on the outer edge of the first region to an interior point of the substrate so as to form a first flap and a second flap,
a first adhesive portion applied to the substrate near the first region such that the first and second flaps each receive part of the first adhesive portion with the slit extending between the respective parts of the first adhesive portion received on the first and second flaps so that the respective parts of the first adhesive portion are positioned directly on opposite sides of the slit, and adjacent the slit, with the slit extending therebetween, and
a second adhesive portion applied to the substrate near the second region, the second adhesive portion being discontinuous with the first adhesive portion,
wherein the first and second flaps are configured to be placed into an overlapping arrangement and adhered together by the first adhesive portion to give the eye patch a generally cupped shape, and wherein the first and second adhesive portions provide two locations, and the eye patch is sized and shaped, for adhering the eye patch to the periorbital tissue located on opposite sides of an eye so as to occlude the eye, wherein the substrate is rounded near the first region and enlarged relative to the second region which is tapered at a tapered tab located near the second region in both a planar and cupped form of the eye patch, and further wherein the first and second flaps include respective facing first and second flap edges, and wherein the substrate includes one or more markings for indicating one or more flap edge alignment positions for placing the first and second flaps into the overlapping arrangement.

\* \* \* \* \*

UNITED STATES PATENT AND TRADEMARK OFFICE
CERTIFICATE OF CORRECTION

PATENT NO. : 10,765,311 B2
APPLICATION NO. : 14/036555
DATED : September 8, 2020
INVENTOR(S) : Barbara Masket Page 1 of 1

It is certified that error appears in the above-identified patent and that said Letters Patent is hereby corrected as shown below:

On the Title Page

Item (57) Abstract
In the last line, change "for adhering the eye patch a patient's face" to --for adhering the eye patch to a patient's face--.

In the Claims

In Claim 9, Column 7, Line 46, change "being discontinuous with the first adhesive portion the substrate being rounded" to --being discontinuous with the first adhesive portion, the substrate being rounded--.

Signed and Sealed this
Seventeenth Day of November, 2020

Andrei Iancu
*Director of the United States Patent and Trademark Office*